United States Patent
Pack et al.

(10) Patent No.: US 9,295,521 B2
(45) Date of Patent: Mar. 29, 2016

(54) STERILE DRAPES FOR X-RAY DEVICES, SYSTEMS CONTAINING THE SAME, AND METHODS FOR USING THE SAME

(71) Applicant: General Electric Company, Schenectady, NY (US)

(72) Inventors: Nathan Allen Pack, Salt Lake City, UT (US); Levi Thomas Rupert, Evansville, IN (US); Jacob Marc Robinson, Provo, UT (US); Dilip Bam Malla, Lumbini (NP); David Weston Richardson, Lafayette, IN (US); Sean Andrew Moore, Canfield, OH (US); Joshua Lindmark, Lexington, KY (US); Anton Edis Bowden, Lindon, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 203 days.

(21) Appl. No.: 14/135,862

(22) Filed: Dec. 20, 2013

(65) Prior Publication Data

US 2015/0173836 A1 Jun. 25, 2015

(51) Int. Cl.
*A61B 6/10* (2006.01)
*A61B 19/08* (2006.01)
*A61B 6/00* (2006.01)

(52) U.S. Cl.
CPC ............... *A61B 19/081* (2013.01); *A61B 6/10* (2013.01); *A61B 6/4441* (2013.01)

(58) Field of Classification Search
CPC .. A61B 19/081; A61B 6/4423; A61B 6/4441; A61B 19/08; A61B 6/10
See application file for complete search history.

(56) References Cited

U.S. PATENT DOCUMENTS

| 5,506,882 | A | 4/1996 | O'Farrell, Jr. et al. | |
|---|---|---|---|---|
| 2004/0025886 | A1 | 2/2004 | Masini | |
| 2005/0047734 | A1* | 3/2005 | Borom | A61B 19/08 385/98 |
| 2008/0147089 | A1 | 6/2008 | Loh et al. | |
| 2009/0232282 | A1* | 9/2009 | Belson | A61B 6/107 378/203 |
| 2011/0214679 | A1* | 9/2011 | Chua | A61B 19/08 128/855 |
| 2013/0025605 | A1 | 1/2013 | Ball et al. | |
| 2015/0124941 | A1* | 5/2015 | Arterson | A61B 6/4441 378/193 |

OTHER PUBLICATIONS

International Search Report and Written Opinion from corresponding PCT application No. PCT/US2014/051451 dated Nov. 25, 2014; 12 pages.

* cited by examiner

*Primary Examiner* — Glen Kao

(57) ABSTRACT

A sterile drape for a C-arm X-ray device includes a slide rail assembly configured to be connected to a C-arm of an X-ray device that extends from a lower portion of the C-arm to an upper portion of the C-arm. The sterile drape further comprises a sterile drape assembly comprising a length of compliant material, the sterile drape assembly configured to be detachably coupled to the upper portion of the C-arm and to the slide rail assembly. The sterile drape also comprises an anchor assembly configured to be connected to the C-arm X-ray device at one end and configured to be connected to the sterile drape assembly at the other end so that the anchor assembly draws the sterile drape assembly along the slide rail assembly as the C-arm is rotated.

19 Claims, 9 Drawing Sheets

STERILE DRAPES FOR X-RAY DEVICES, SYSTEMS CONTAINING THE SAME, AND METHODS FOR USING THE SAME

FIELD

This application relates generally to X-ray equipment. More specifically, this application relates to sterile drapes for C-arm X-ray devices that allow users to easily maintain sterility in a surgical field as the C-arm is rotated or moved around a patient, systems containing such drapes, and methods of using such drapes.

BACKGROUND

A typical X-ray imaging system comprises an X-ray source and an X-ray detector. X-rays emitted from the X-ray source can impinge on the X-ray detector and provide an X-ray image of an object or subject that is placed between the X-ray source and the detector. In one type of X-ray imaging system, a fluoroscopic imaging system, the X-ray detector is often an image intensifier or a flat panel digital detector.

Fluoroscopic imaging systems can be either fixed or mobile. For instance, fixed fluoroscopic imaging systems often include a gantry that is secured to a floor, wall, or ceiling. Additionally, mobile fluoroscopic imaging systems are movable so that they can be used in a variety of clinical environments, such as radiology and surgery departments of a medical facility. The mobile fluoroscopic imaging systems may include a C-arm, G-arm, O-arm, L-arm, or another imaging arm or gantry assembly. A mobile fluoroscopic imaging system may also be configured as a mini C-arm.

The C-arm assembly of a fluoroscopic imaging system moves relative to the subject in order to acquire images from multiple angles and can be manually repositioned to generate images from different angles. In some configurations, the C-arms are connected to one end of a movable arm so the C-arm can often be raised and lowered, be moved from side to side, and/or be rotated about one or more axes of rotation. Accordingly, the C-arms can be moved and reoriented to allow X-ray images to be taken from several different positions and angles and of one or more portions of a patient, without requiring the patient to be frequently repositioned. In situations where a sterile field is required, such as in surgery, sterile drape systems are often used to cover the C-arm to maintain the sterile field when it is needed.

SUMMARY

This application describes sterile drapes for C-arm X-ray devices that allow users to easily maintain sterility in a surgical field as the C-arm is rotated or moved around a patient. The sterile drape contains a slide rail assembly configured to be connected to a C-arm of an X-ray device so as extend from a lower portion of the C-arm to an upper portion of the C-arm, a sterile drape assembly comprising a length of compliant material, the sterile drape assembly configured to be detachably coupled to the upper portion of the C-arm and to the slide rail assembly, and an anchor assembly configured to be connected to the X-ray device at one end and configured to be connected to the sterile drape assembly at the other end so that the anchor assembly draws the sterile drape assembly along the slide rail assembly as the C-arm is rotated. The sterile drape is connected to the X-ray device so that one end of the sterile drape assembly remains in substantially the same position regardless of the movement of the C-arm.

BRIEF DESCRIPTION OF THE DRAWINGS

The following description can be better understood in light of the Figures, in which.

Figure 1:
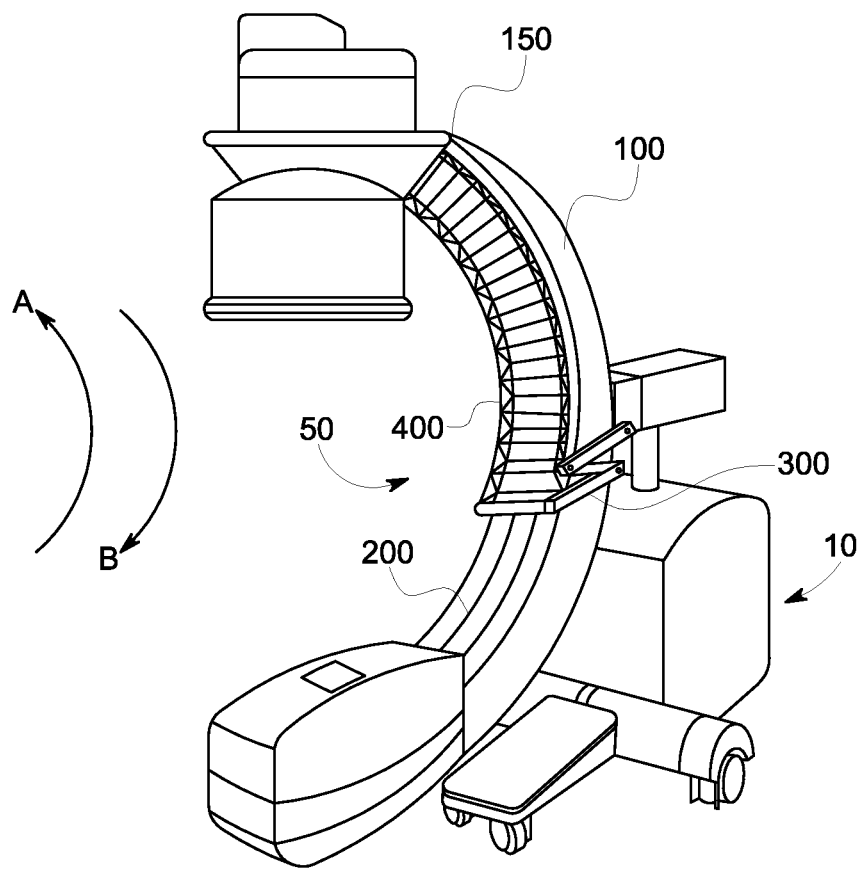
FIG. 1 shows a front perspective view of some embodiments of a sterile drape system for a C-arm.

The Figures illustrate specific aspects of the sterile drapes for C-arm X-ray devices and methods for making and using such devices. Together with the following description, the Figures demonstrate and explain the principles of the methods and structures produced through these methods. In the drawings, the thickness of layers and regions are exaggerated for clarity. The same reference numerals in different drawings represent the same element, and thus their descriptions will not be repeated. As the terms on, attached to, or coupled to are used herein, one object (e.g., a material, a layer, a substrate, etc.) can be on, attached to, or coupled to another object regardless of whether the one object is directly on, attached, or coupled to the other object or there are one or more intervening objects between the one object and the other object. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

DETAILED DESCRIPTION

The following description supplies specific details in order to provide a thorough understanding. Nevertheless, the skilled artisan will understand that the described collapsible sterile drape system and associated methods of making and using the devices can be implemented and used without employing these specific details. Indeed, the collapsible sterile drape system and associated methods can be placed into practice by modifying the described devices and methods and can be used in conjunction with any other apparatus and techniques conventionally used in the industry. For example, while the description below focuses on methods for making and using the collapsible sterile drape system for mini C-arms, they can be used with virtually any other type of X-ray equipment, including C-arms, G-arms, O-arms, and L-arms.

The sterile drape system (or just drape system) can be used to maintain sterility in a surgical field as a C-arm of an X-ray device is rotated or moved around a patient. FIG. 1 shows some embodiments of a drape system that can be used with an X-ray device containing a C-arm. In FIG. 1, the drape system 50 can be positioned on—or mounted to—the C-arm positioning device (C-arm) 100 of an X-ray device 10. In the illustrated embodiments, the C-arm may be part of a mobile X-ray device 10.

The drape system 50 comprises a drape slide rail assembly (slide rail) 200, a drape anchor assembly (anchor assembly) 300, and a collapsible, sterile drape assembly (drape assembly) 400. The slide rail 200 can be attached to an inner circumference of the C-arm 100 and configured to extend along this inner circumference and to run parallel to it. The anchor assembly 300 extends alongside the C-arm 100 with a proximal end adjacent to the slide rail 200.

In the illustrated embodiments, the drape system 50 maintains sterility in a surgical field by maintaining the unsterile inner circumference of the C-arm 100 covered with the sterile drape assembly 400. Since the drape assembly 400 can expand or contract as the C-arm 100 is rotated, the drape assembly 400 maintains the unsterile inner circumference of the C-arm 100 isolated from the sterile surgical field. The drape assembly 400 is connected or attached to the C-arm 100 using the anchor assembly 300. So as the C-arm 100 rotates in the direction of arrow A, the drape assembly 400 expands as it is drawn along the slide rail 200 by the anchor assembly 300. As the drape assembly 400 expands along the slide rail 200, the sterile drape assembly covers the unsterile inner circumference of the C-arm 100 and maintains the sterility of the surgical field. When the C-arm 100 is rotated in the direction of arrow B, the drape assembly 400 contracts as it moves along the slide rail 200 and is anchored by the anchor assembly 300. As the drape assembly 400 contracts along the slide rail 200, the sterile drape assembly is also maintained within the sterile surgical field.

In some embodiments, the drape assembly 400 comprises a length of folded, compliant sterile medical grade material that can be connected at one end to an upper end 150 of the inner circumference of the C-arm 100 and is connected at another end to the proximal end of the anchor assembly 300. The drape assembly 400 can be configured to move along the slide rail 200 with the slide rail 200 acting as a guide. The drape assembly 400 can be configured such that folds of the drape assembly 400 allow the drape assembly 400 to expand or contract in an accordion-like fashion along the length-wise dimension of the compliant sterile medical grade material. The drape assembly 400 can be configured to be compliant so that the drape assembly 400 moves along the slide rail 200 and also so that the drape assembly 400 conforms to the inner circumference of the C-arm 100.

Figure 2A:
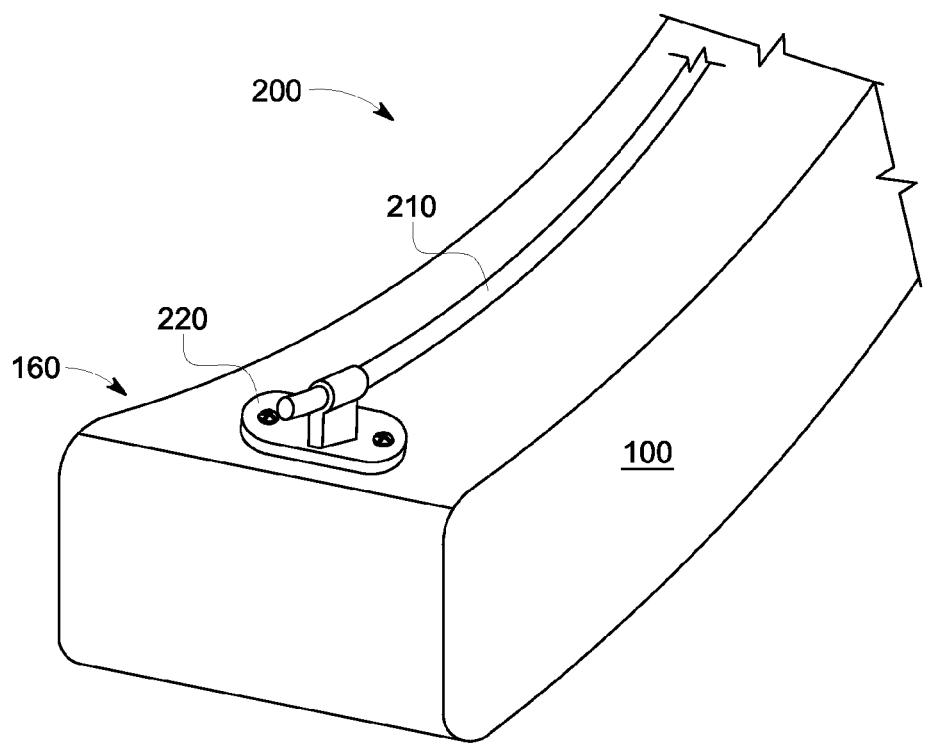
FIGS. 2A and 2B show side perspective and cross-sectional views of some embodiments of a slide rail assembly.
Figure 2B:
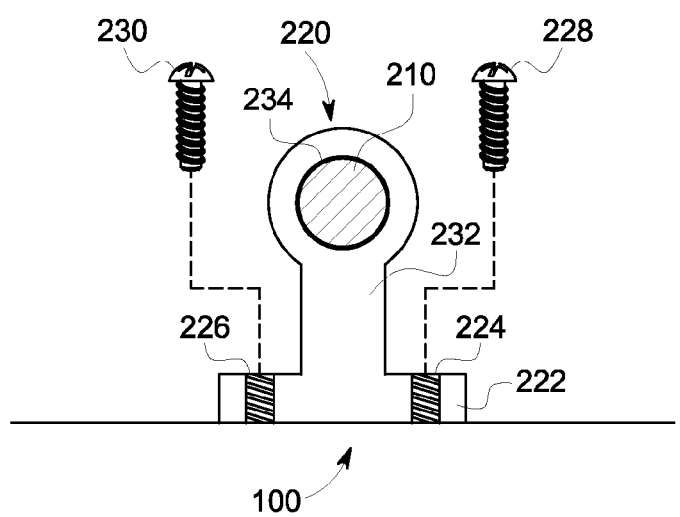

FIGS. 2A and 2B illustrate some embodiments of the components and arrangements of the slide rail 200 of the drape system 50. In these embodiments, the slide rail 200 comprises a slide rod 210 and a pair of slide anchors 220. The pair of slide anchors 220 connects the slide rod 210 to the C-arm 100. The slide rail 200 can be configured to extend along the inner circumference of the C-arm from the upper end 150 to a lower end 160 along the entire length of the inner circumference of the C-arm. In some configurations, the pair of slide anchors 220 can be arranged such that one slide anchor connects the slide rail 200 to the C-arm adjacent to the upper end 150 and such that another anchor connects the slide rail to the other end of the inner circumference of the C-arm 100. In other configurations, the pair of slide anchors 220 can be configured to connect the slide rail 200 to the C-arm 100 such that the slide rod 210 is oriented parallel to the inner circumference of the C-arm 100. In yet other configurations, the pair of slide anchors 220 can be configured to connect the slide rail 200 to the inner circumference of the C-arm 100 such that the slide rod 210 is arranged approximately midway between the lengthwise edges of the inner circumference of the C-arm 100. In further configurations, the pair of slide anchors 220 can be configured to maintain the slide rod 210 elevated from and substantially parallel to the inner circumference of the C-arm 100.

FIG. 2B illustrates some embodiments of the components and arrangements of the pair of slide anchors 220. FIG. 2B shows a cutaway view of one slide anchor 220 as viewed from the end of the C-arm 100. As shown in the embodiments depicted in FIG. 2B, the slide anchor 220 comprises a mounting base 222, an elevating flange 232, and a receiving aperture 234. The mounting base 222 abuts the inner circumference of the C-arm 100 and comprises mounting holes 224, 226. Fasteners 228, 230 extend through the mounting holes 224, 226 and connect the mounting base 222 to the inner circumference of the C-arm 100. The elevating flange 232 extends from the mounting base 222 on one end and encompasses the receiving aperture 234 on the other end. The receiving aperture 234 can be configured to couple to an end of the slide rod 210. In some embodiments, the receiving aperture 234 can be configured such that the slide rod 210 extends entirely through the receiving aperture 234 while in other embodiments the slide rod 210 only partially extends through the receiving aperture 234. While FIG. 2B illustrates some embodiments of the slide anchors, other methods of anchoring the slide rod 210 to the C-arm 100 can be used.

The slide rail 200 may comprise plastic, metal, or any number of other types of material. In some configurations, the slide rod 210 may be made of a low friction material, such as aluminum.

The slide rod 210 and slide anchor 220 may have any number of different shapes and orientations. For example, the slide anchor 220 can comprise a single fastener or a plurality of fasteners, or the height of the elevating flange 232 can be raised or lowered as necessary for the overall arrangement and configuration of the drape system 50. As another example, the slide rod 210 may be substantially circular, elliptical, rectangular, or flat shaped in cross-section. In other embodiments, the slide rod 210 comprises a mounting flange that runs the length of the slide rod 210 to connect the slide rod 210 to the inner circumference of the C-arm 100. In some embodiments, the slide rod 210 can be replaced with a guide channel that runs the length of the inner circumference of the C-arm 100 to guide the drape assembly 400. In yet other embodiments, the slide rail 200 comprises any number of slide rods 210 and/or slide anchors 220. In other embodiments, the slide rail 200 can be configured to be disposable. In other embodiments, the slide rail 200 can be configured to connect to the C-arm 100 magnetically and/or by adhesive. Thus, the slide rail 200 can be configured to be easily removed and easily replaced to allow for cleaning and/or sterilization of the drape system 50 and/or the X-ray device 10.

Figure 3A:
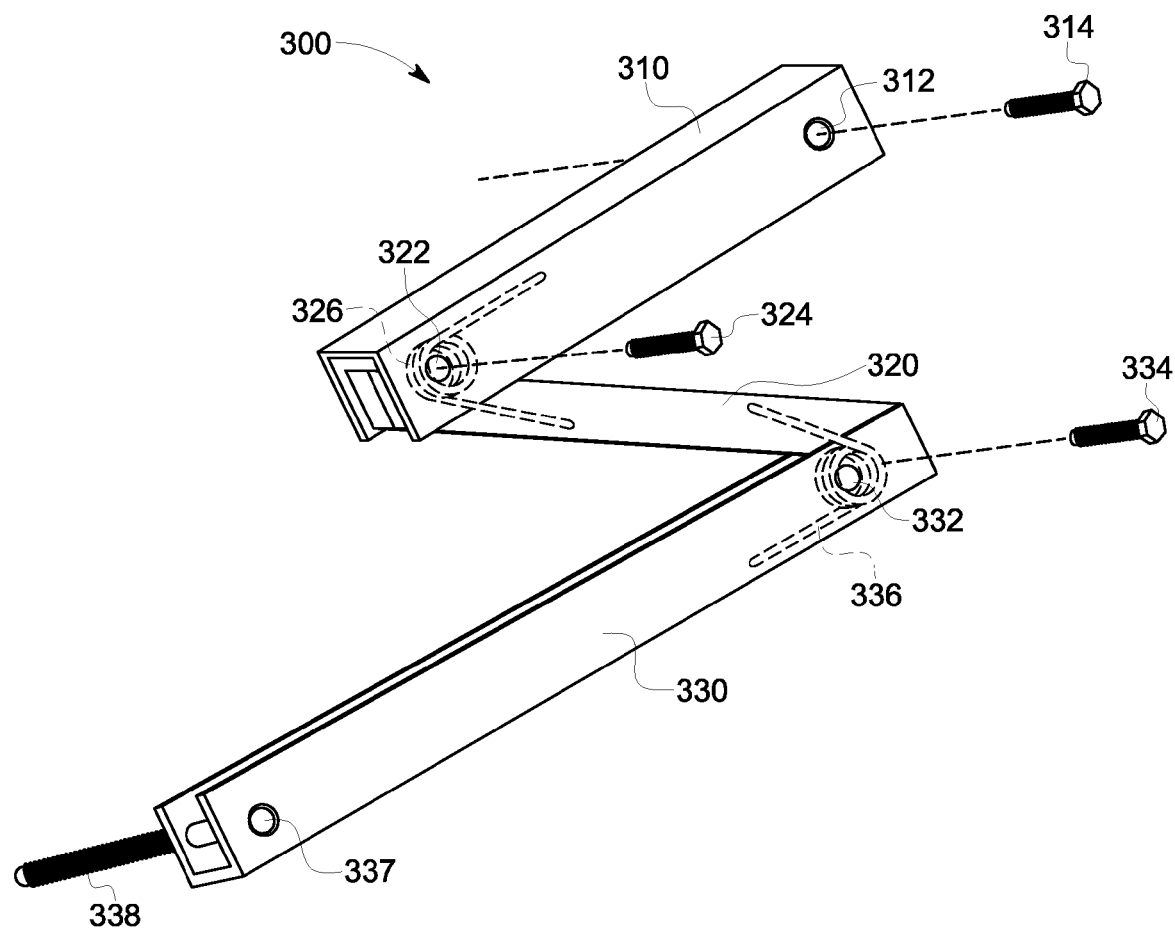
FIGS. 3A, 3B, and 3C show side perspective and side views of some embodiments of a drape anchor assembly.
Figure 3B:
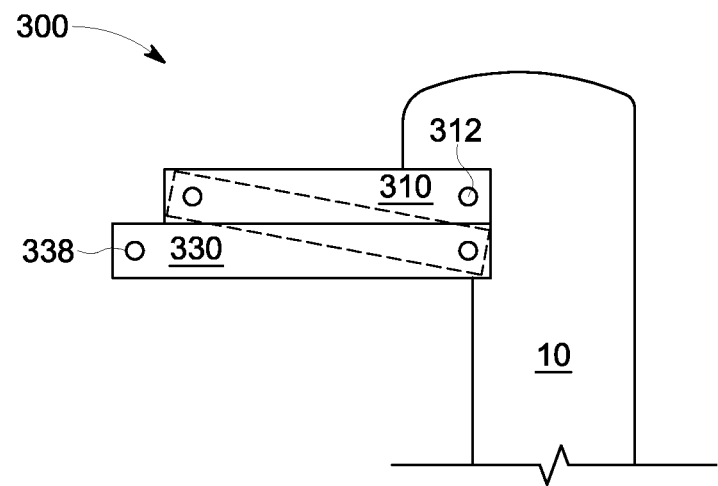
Figure 3C:
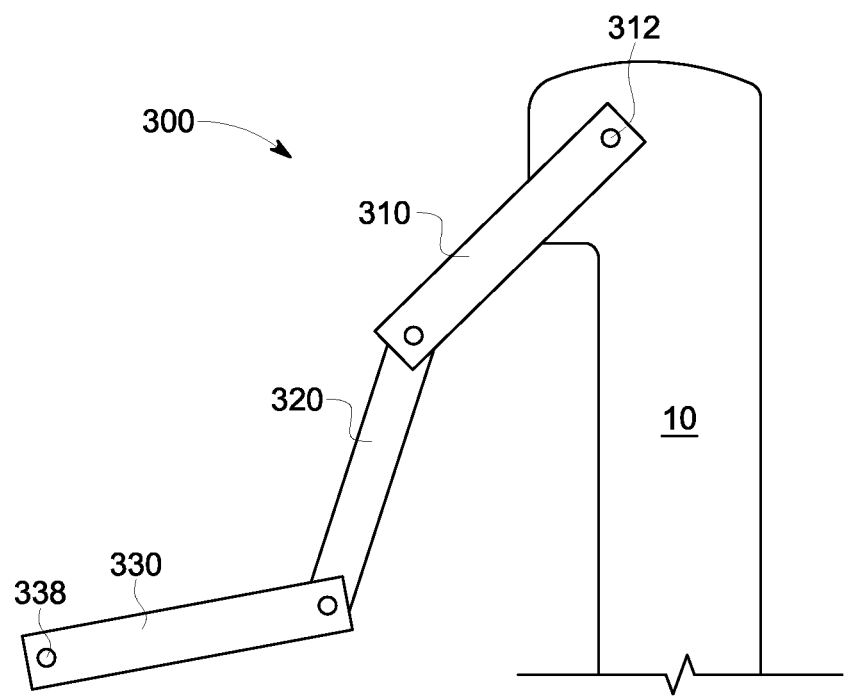

FIGS. 3A, 3B, and 3C illustrate some embodiments of the components and arrangements of the second component of the anchor assembly 300 of the drape system 50. As shown in FIG. 3A, the anchor assembly 300 comprises a first arm 310, a second arm 320, and a third arm 330. The proximal end of the first arm 310 can be rotatably coupled to the desired part of the X-ray device 10 via a mounting hole 312 on the proximal end of the first articulating arm 310 using a fastener 314. The distal end of the first arm 310 can then be rotatably coupled to the proximal end of the second arm 320 via a hole 322 and a fastener 324. In some configurations, the rotatable coupling between the distal end of the first arm 310 and the proximal end of the second arm 320 can include a spring 326 to exert tension to maintain the rotatable coupling in a retracted position. The distal end of the second arm 320 can be rotatably coupled to the proximal end of the third arm 330 via a hole 332 and a fastener 334. In some configurations, the rotatable coupling between the distal end of the second arm 320 and the proximal end of the third arm 330 can include a spring 336 to exert tension to maintain the rotatable coupling in a retracted position. A drape mounting rod 338 can be secured to the distal end of the third arm via a hole 337 that is configured to secure the end of the drape mounting rod 338. The drape mounting rod 338 can then be connect to an end of the drape assembly 400 to allow the drape assembly 400 to be drawn along the slide rail 200.

FIGS. 3B and 3C show some embodiments of the fully retracted and fully extended positions of the anchor assembly. As shown in FIG. 3B, springs 326 and 336 exert tension to hold the anchor assembly 300 in a fully retracted position. While in the fully retracted position, the drape mounting rod 338 is positioned closest to the X-ray device 10. The anchor assembly 300 is configured to draw the drape assembly 400 along the slide rail 200 as the C-arm 100 moves. As the C-arm 100 is moved, the slide rail 200 may translate away from the X-ray device 10. As shown in FIG. 3C, the anchor assembly 300 can transition from the fully retracted position to the fully extended position as the C-arm 100 moves through a full range of motion. As the anchor assembly 300 transitions from the fully retracted position to the fully extended position, the drape mounting rod 338 moves to a farthest position from the X-ray device 10. An articulating motion of the anchor assembly 300 as it transitions from a fully retracted to a fully extended position allows the anchor assembly 300 to draw the drape assembly 400 evenly and smoothly along the slide rail 200. Likewise, the articulating motion of the anchor assembly 300 as it transitions from a fully extended to a fully retracted position allows the anchor assembly 300 to draw the drape assembly 400 evenly and smoothly along the slide rail 200. Thus, the anchor assembly 300 can draw the drape assembly 400 along the slide rail 200 when it is connected to a variety of shapes and configuration of the C-arm 100 or other shaped arms, including G-arms, O-arms, and L-arms.

The anchor assembly 300 may comprise plastic, metal, or any number of other types of material. By way of example only, the first, second, and third arms may be made of aluminum. The components of the anchor assembly 300 may have any number of different shapes and orientations. For example, the anchor assembly 300 may comprise only two arms or may comprise more than three arms. In another example, the anchor assembly 300 may comprise a single arm configured to slideably extend through a slide fitting that is pivotally connected to the X-ray machine. The single-armed anchor assembly 300 embodiments of this type may further comprise a spring to exert tension on the single arm.

The anchor assembly 300 may have other configurations. The anchor assembly 300 may comprise one or more hydraulic pistons and/or compressed air pistons to exert tension on the anchor assembly 300 to draw the drape assembly 400 along the slide rail 200. In yet other embodiments, a single arm of the anchor assembly 300 can be replaced with one or more hydraulic pistons and/or compressed air pistons. In alternate embodiments, the anchor assembly can be connected to a structure that is proximate to the C-arm 100. In yet another embodiment, the anchor assembly 300 can be configured to be disposable or to connect to the X-ray device magnetically and/or by adhesive. The anchor assembly 300 can also be configured to be easily removed and replaced to allow for cleaning and/or sterilization of the drape system 50 and/or the X-ray device 10.

The drape mounting rod 338 may have any number of different shapes and orientations. For example, the drape mounting rod 338 may comprise an elongated flange. In other embodiments, the drape mounting rod 338 may be replaced with a clip and/or fastener. In alternate embodiments, the drape mounting rod 338 may be replaced with an extended surface that is configured to selectably couple the drape assembly 400 with an adhesive, adhesive tape, hook and loop fastener, and/or other suitable fastener. In yet another embodiment, the drape mounting rod 338 can be configured to be disposable.

Figure 4A:
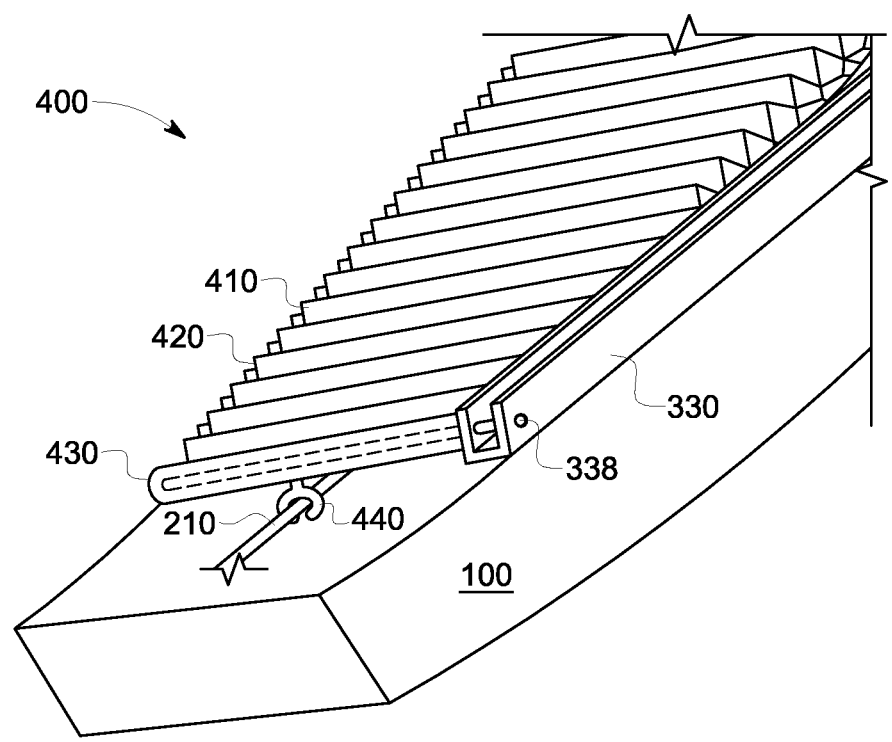
FIGS. 4A, 4B, and 4C show side perspective and top views of some embodiments of a sterile drape assembly.
Figure 4B:
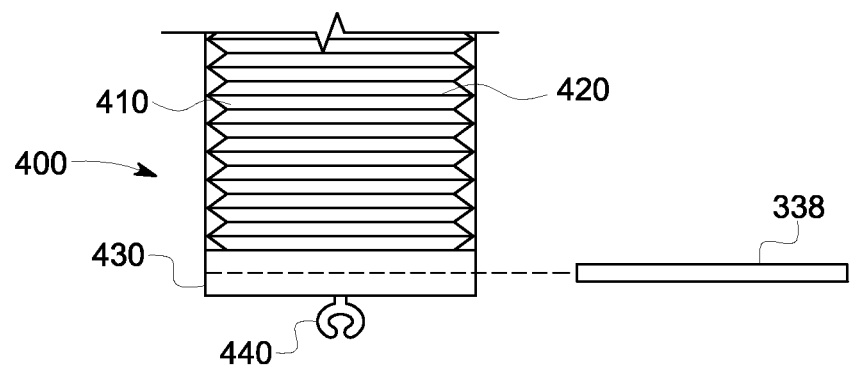
Figure 4C:
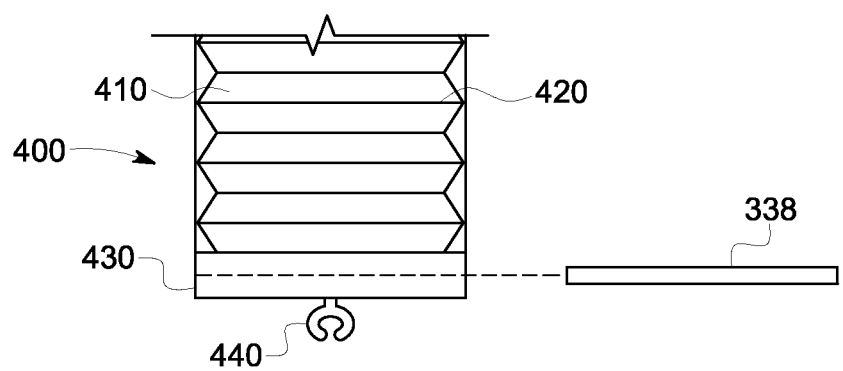

FIGS. 4A, 4B, and 4C illustrate some embodiments of the components and arrangements of the drape assembly 400 of the drape system 50. In the embodiments shown in FIG. 4A, the drape assembly 400 comprises a compliant material 410, a pocket 430, and a retaining clip 440. The compliant material 410 comprises a length of sterile medical-grade material that is configured with accordion-like folds 420 that allow the drape assembly 400 to expand or contract as the drape assembly is drawn along the slide rail 200. The folds 420 can be configured to be perpendicular to a direction of movement of the drape assembly 400 along the slide rail 200. The pocket 430 can be configured to receive the drape mounting rod 338 to selectably couple one end of the drape assembly 400. The pocket 430 can be formed by folding an end of the compliant material 410 and attaching an outer edge of the compliant material 410 to a body of the compliant material 410. The outer edge can be attached to the body with adhesive, by hook and loop fastener, and/or by sewing. Another end of the compliant material 410 can configured to attach an upper end 150 of the inner circumference of the C-arm 100. The retaining clip 440 can be attached to the pocket 430 and is configured to detachably couple to the slide rod 210. In some embodiments, a plurality of retaining clips 440 are attached to the compliant material 410 to guide the drape assembly 400 along the slide rail 200.

FIGS. 4B and 4C show some embodiments of the fully contracted and fully expanded positions of the drape assembly 400. As shown in FIG. 4B, the drape mounting rod 338 is received into the pocket 430 and the retaining clip 440 is positioned to detachably couple the slide rail 200. When the drape assembly 400 is in a contracted position, the folds 420 in the compliant material 410 accommodate the full length of the compliant material 410 into a contracted space. As shown in FIG. 4C, when the drape assembly 400 is in an expanded position, the folds 420 in the compliant material 410 allow the full length of the compliant material to fill an expanded space. Thus, the drape assembly 400 can expand or contract along the slide rail 200 when it is connected to a variety of shapes and configurations of the C-arm 100 or other shaped arms, including G-arms, O-arms, and L-arms.

The compliant material 410 may comprise paper, plastic-backed paper, metal-backed paper, cardboard, plastic, fabric, metal foil, or any number of other types of material. By way of example only, the compliant material 410 may be made of sterile medical grade, plastic-backed paper. The drape assembly 400 may have any number of different shapes and orientations. For example, the compliant material 410 may be configured to cover all or part of three sides of the C-arm with the compliant material 410 forming a U-shape. In other embodiments, the compliant material 410 may be configured to partially or completely envelope the C-arm 100.

Likewise, the folds 420 may have any number of different shapes and orientations. For example, the folds 420 may be configured in a diagonal cross-hatch pattern. In other embodiments, the folds 420 may be configured in a hexagonal, honeycomb pattern. In yet other embodiments, the folds 420 may be configured in a fashion similar to an expanding Chinese paper lantern. Alternate embodiments of the folds 420, such as other typical or known folding patterns are also contemplated.

The retaining clip 440 may have any number of different shapes and orientations and there are many ways by which the compliant material 410 can be detachably coupled to the slide rail 200. For example, the retaining clip 440 can comprise an open-ended plastic ring that is configured to detachably and slideably couple the slide rail 200. In other embodiments, the retaining clip 440 can be configured as an open-ended hook configured to detachably and slideably couple the slide rail 200. Alternate embodiments of the retaining clip 440 are also contemplated.

The end of the compliant material 410 can be attached to the upper end 150 of the C-arm 100 using any mechanism. In some embodiments, the end of the compliant material 410 is configured to attach an upper end 150 of the inner circumference of the C-arm 100 with an adhesive, adhesive tape, hook and loop fastener, and/or other suitable fastener. In yet other embodiments, the compliant material 410 can be attached to the upper end 150 with a second pocket and a second drape mounting rod.

The drape assembly can have other configurations. In some embodiments, the drape assembly 400 can be configured to be disposable. In other embodiments, the drape assembly 400 is configured to be sterilized and reused. In another embodiment, the drape assembly 400 can be configured to be easily removed and easily replaced to allow for cleaning and/or sterilization of the drape system 50 and/or the X-ray device 10.

Figure 5A:
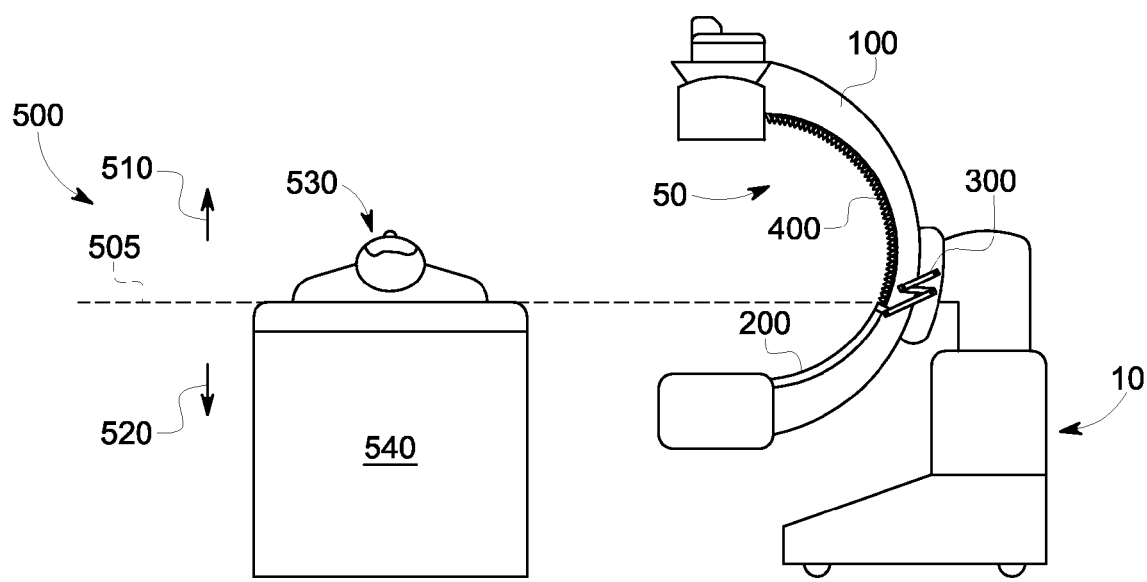
FIG. 5A shows a side view of some embodiments of the sterile drape system in relation to a surgical field.
Figure 5B:
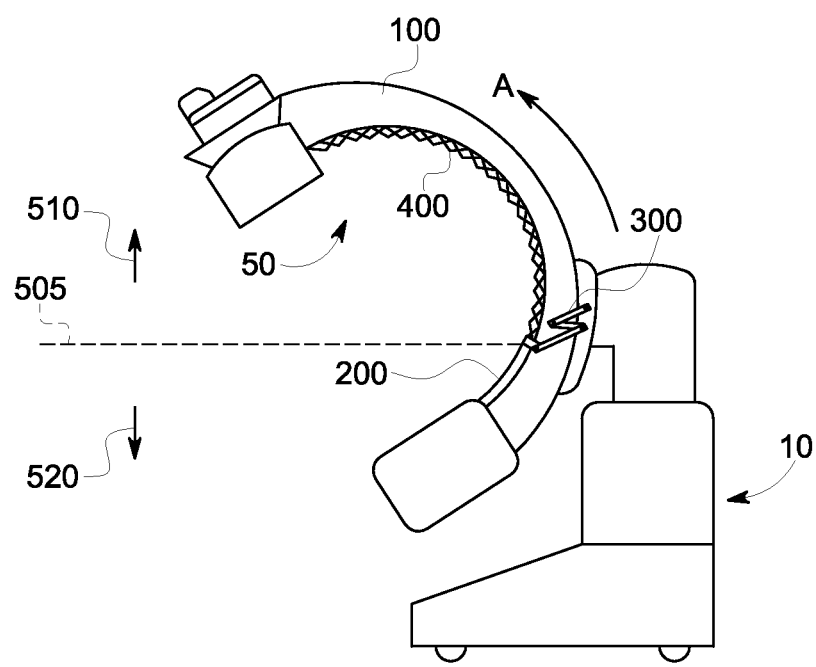
FIGS. 5B and 5C show side views of some embodiments of a sterile drape system in relation to rotation of a C-arm of an X-ray device.
Figure 5C:
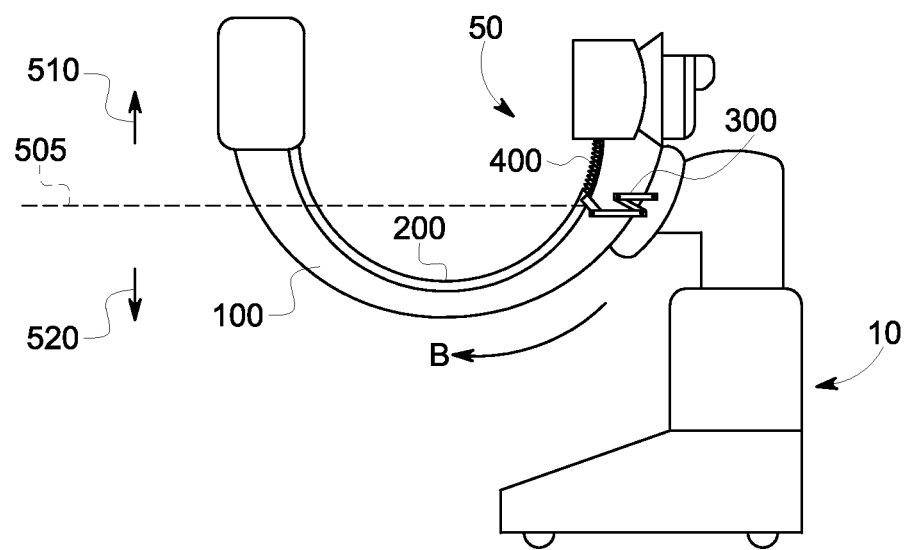

FIGS. 5A, 5B, and 5C illustrate side views of some embodiments of the assembled drape system 50 in relation to a surgical field 500. In these embodiments, the surgical field 500 can be divided along a sterility plane 505 into a sterile field 510 and a non-sterile field 520. A patient 530 lies on an operating table 540 and substantially defines a height of the sterility plane 505. An upper surface of the operating table 540 defines the sterility plane 505 with the sterile field 510 encompassing the area above the sterility plane 505 and the non-sterile field 520 encompassing the area below the sterility plane 505. As needed, the X-ray device 10 can be moved into the surgical field 500 to perform and/or monitor any desired surgical procedure. In some embodiments, the anchor assembly 300 can be configured to be about even with the sterility plane 505. As the C-arm 100 rotates about the patient to perform and/or monitor procedures, the drape system 50 maintains the sterility in the surgical field 500. The drape system 50 allows the drape assembly 400 to expand or contract to isolate a portion of the C-arm as it rotates into or out of the sterile field 510. The anchor assembly 300 draws the drape assembly 400 along the slide rail 200 as the drape assembly 400 expands and contracts to cover the C-arm 100. The drape system 50 also prevents the drape assembly 400 from entering the non-sterile field 520.

As shown in FIG. 5B, the drape system 50 allows the drape assembly 400 to expand as the C-arm 100 is rotated in the direction of the arrow A. As the C-arm 100 rotates in the direction of the arrow A, the anchor assembly 300 draws the drape assembly 400 along the slide rail 200. The drape assembly 400 expands to isolate an additional portion of the C-arm 100 that enters the sterile field 510 as the C-arm 100 rotates. The articulating motion of the anchor assembly 300 also maintains tension on the drape assembly 400 to prevent slack. The articulating motion of the anchor assembly 300 also allows the drape assembly 400 to track along the slide rail 200 to substantially match the shape of the inner circumference of the C-arm 100.

FIG. 5C shows the drape assembly 400 contracting as the C-arm 100 rotates in the direction of the arrow B. As the C-arm rotates in the direction of the arrow B, the anchor assembly 300 draws the drape assembly along the slide rail 200. The articulating motion of the anchor assembly 300 maintains tension on the drape assembly 400 as it contracts. The articulating motion of the anchor assembly 300 also prevents the drape assembly 400 from entering the non-sterile field 520. Thus, whether the C-arm 100 rotates in the direction of arrow A or in the direction of arrow B, the portion of the C-arm 100 in the sterile field 510 is isolated from the surgical field and the drape assembly 400 can be prevented from entering the non-sterile field 520. Therefore, the drape system 50 allows the sterility of the surgical field 500 to be maintained throughout the full range of motion of the C-arm 100 and at any stopping point there between.

The drape system 50 may have any number of different shapes and orientations. In some embodiments, the anchor assembly 300 can be connected to a surface proximate to the C-arm 100 that is not the X-ray device 10. In other embodiments, the drape system 50 can be configured such that the location and orientation of the drape mounting rod 338 may be adjustable to accommodate different orientations of the sterility plane 505. Thus, the drape system 50 can be configured to be adjustable to accommodate a sterility plane 505 of different heights or different angles with respect to the operating table 540. In another embodiment, the slide rail 200 may be configured to be integral with the drape assembly 400. In other embodiments, the drape system 50 can be configured to be compatible with other sterility measures such as surgical barriers, surgical drapes, surgical cloths, etc. In yet other embodiments, the drape system 50 can be configured to be disposable or to connect to the X-ray device magnetically and/or by adhesive. In still other embodiments, the drape system 50 is configured to be easily removed and easily replaced to allow for cleaning and/or sterilization of the drape system 50 and/or the X-ray device 10.

The drape system 50 can have any configuration that allows it to easily maintain sterility in a surgical field as the C-arm of an X-ray device is rotated or moved around a patient. For example, the drape system 50 can comprise one or more support structure covers, handles, power supplies (e.g., internal and/or external), control devices, actuators, brake systems, displays, monitors, workstations and/or other components.

The drape system 50 can be used to maintain sterility in the surgical field 500 during any surgical procedure. By way of example, an operator can use the drape system 50 by detachably connecting an unused sterile drape assembly 400 to the upper end 150 of the C-arm, selectably engaging the retaining clip 440 onto the slide rod 210, and fitting the drape mounting rod 338 into the pocket 430. With the sterile drape assembly 400 in place, the operator can rotate the C-arm as needed while maintaining sterility of the surgical field 500. In some embodiments, the operator can use the drape system 50 by detaching the used sterile drape assembly 400 from the upper end 150 of the C-arm, selectably disengaging the retaining clip 440 from the slide rod 210, and removing the drape mounting rod 338 from the pocket 430.

The drape system 50 described herein has several useful features. First, because the anchor assembly 300 maintains the end of the drape assembly 400 at about the level of the sterility plane 505, the drape assembly 400 can be prevented from expanding into the non-sterile field 520 and becoming contaminated. Also, the sterile drape assembly 400 can be prevented from expanding into the non-sterile field 520 and then being drawn back into the sterile field 510 and potentially contaminating the sterile field 510. Accordingly, the sterility of the drape assembly 400 can be maintained.

Second, the drape system 50 does not comprise any loose bag coverings or drapes that may interfere with the transport and/or positioning of the X-ray device 10 within the surgical field 500. The absence of loose bag coverings or drapes can also prevent interference with the rotation of the C-arm 100 during performance and/or monitoring of surgical procedures.

Third, the drape system 50 can be configured to allow for the easy placement and removal of the drape assembly 400. Thus, the drape system 50 can be easily and quickly prepared for use in the surgical field 500 and easily and quickly attended to after use. This ease of use saves time and resources and reduces time needed to prepare the surgical field 500 and reduces time needed clean up the surgical field 500 after use. Also, because the drape system 50 can be easily prepared and easily cleaned up, the risk of nosocomial infection is reduced.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

We claim:

1. A sterile drape for an X-ray device, comprising:
   a slide rail assembly configured to be connected to a C-arm of an X-ray device so as extend from a lower portion of the C-arm to an upper portion of the C-arm;
   a sterile drape assembly comprising a length of compliant material, the sterile drape assembly configured to be detachably coupled to the upper portion of the C-arm and to the slide rail assembly; and
   an anchor assembly configured to be connected to the X-ray device at one end and configured to be connected to the sterile drape assembly at the other end so that the anchor assembly draws the sterile drape assembly along the slide rail assembly as the C-arm is rotated.

2. The sterile drape of claim 1, wherein the slide rail assembly comprises a slide rod and a plurality of slide anchors configured to mount the slide rod to the C-arm.

3. The sterile drape of claim 1, wherein the anchor assembly comprises a first articulating arm with a proximal end coupled to the X-ray device with a rotatable coupling.

4. The sterile drape of claim 3, wherein the anchor assembly further comprises:
   a second articulating arm coupled by a proximal end to a distal end of the first articulating arm with a rotatable coupling; and
   a third articulating arm coupled by a proximal end to a distal end of the second articulating arm with a rotatable coupling.

5. The sterile drape of claim 4, wherein the anchor assembly is further configured to maintain a distal end of the third articulating arm at a consistent level to maintain a sterile field.

6. The sterile drape of claim 1, wherein the anchor assembly further comprises a drape mounting rod to detachably couple the anchor assembly to the sterile drape assembly.

7. The sterile drape of claim 1, wherein the compliant material expands or contracts as the sterile drape assembly is drawn along the slide rail assembly.

8. The sterile drape of claim 1, wherein the sterile drape assembly further comprises:
   a pocket configured to detachably couple the sterile drape assembly to the anchor assembly; and
   a retaining clip configured to detachably and slideably couple the sterile drape assembly to the slide rail assembly.

9. The sterile drape of claim 1, wherein the sterile drape assembly is configured for a single use.

10. An X-ray system, comprising:
    an X-ray device containing a movable C-arm; and
    a sterile drape attached to the X-ray device, comprising:
      a slide rail assembly connected to the C-arm that extends from a lower portion of the C-arm to an upper portion of the C-arm;
      a sterile drape assembly comprising a length of compliant material, the sterile drape assembly detachably coupled to the upper portion of the C-arm and to the slide rail assembly; and
      an anchor assembly connected to the X-ray device at one end and connected to the sterile drape assembly at the other end so that the anchor assembly draws the sterile drape assembly along the slide rail assembly as the C-arm is rotated.

11. The X-ray system of claim 10, wherein the slide rail assembly comprises a slide rod and a plurality of slide anchors configured to mount the slide rod to the C-arm.

12. The X-ray system of claim 10, wherein the anchor assembly comprises a first articulating arm with a proximal end coupled to the X-ray device with a rotatable coupling.

13. The X-ray system of claim 12, wherein the anchor assembly further comprises:
    a second articulating arm coupled by a proximal end to a distal end of the first articulating arm with a rotatable coupling; and
    a third articulating arm coupled by a proximal end to a distal end of the second articulating arm with a rotatable coupling.

14. The X-ray system of claim 13, wherein the anchor assembly is further configured to maintain a distal end of the third articulating arm at a consistent level to maintain a sterile field.

15. The X-ray system of claim 10, wherein the compliant material expands or contracts as the sterile drape assembly is drawn along the slide rail assembly.

16. A method of maintaining a sterile field proximate to an X-ray device during a surgical procedure, comprising:
    providing the X-ray device containing a movable C-arm; and
    connecting a sterile drape to the X-ray device, the sterile drape comprising:
      a slide rail assembly connected to the C-arm that extends from a lower portion of the C-arm to an upper portion of the C-arm;
      a sterile drape assembly comprising a length of compliant material, the sterile drape assembly detachably coupled to the upper portion of the C-arm and to the slide rail assembly; and
      an anchor assembly connected to the X-ray device at one end and connected to the sterile drape assembly at the other end so that the anchor assembly draws the sterile drape assembly along the slide rail assembly as the C-arm is rotated;

moving the C-arm so that one end of the sterile drape assembly remains in substantially the same position regardless of the movement of the C-arm.

17. The method of claim 16, wherein the anchor assembly comprises a first articulating arm with a proximal end coupled to the X-ray device with a rotatable coupling, a second articulating arm coupled by a proximal end to a distal end of the first articulating arm with a rotatable coupling, and a third articulating arm coupled by a proximal end to a distal end of the second articulating arm with a rotatable coupling.

18. The method of claim 16, wherein the anchor assembly maintains the sterile drape assembly at a substantially consistent level to maintain the sterile field.

19. The method of claim 16, wherein the compliant material expands or contracts as the sterile drape assembly is drawn along the slide rail assembly.

* * * * *